US00PP28069P3

(12) United States Plant Patent
Kerley et al.

(10) Patent No.: US PP28,069 P3
(45) Date of Patent: May 30, 2017

(54) ***PETUNIA* PLANT NAMED 'KERLATTE'**

(50) Latin Name: *Petunia×atkinsiana*
Varietal Denomination: Kerlatte

(71) Applicants: David William Kerley, Over (GB); Priscilla Grace Kerley, Over (GB); Timothy Edward Kerley, Longstanton (GB)

(72) Inventors: David William Kerley, Over (GB); Priscilla Grace Kerley, Over (GB); Timothy Edward Kerley, Longstanton (GB)

( * ) Notice: Subject to any disclaimer, the term of this patent is extended or adjusted under 35 U.S.C. 154(b) by 66 days.

(21) Appl. No.: 14/756,468

(22) Filed: Sep. 8, 2015

(65) Prior Publication Data

US 2017/0071109 P1 Mar. 9, 2017

(51) Int. Cl.
*A01H 5/02* (2006.01)

(52) U.S. Cl.
USPC ..... Plt./356.1

(58) Field of Classification Search
USPC ..... Plt./356.1
See application file for complete search history.

*Primary Examiner* — Keith Robinson
(74) *Attorney, Agent, or Firm* — C. A. Whealy

(57) ABSTRACT

A new and distinct cultivar of *Petunia* plant named 'Kerlatte', characterized by its mounding plant habit becoming more outwardly spreading with development; freely branching habit; moderately vigorous growth habit; early and freely flowering habit; medium-sized pale cream-colored flowers with dark purple-colored centers and venation; and good garden performance.

3 Drawing Sheets

Botanical designation: *Petunia×atkinsiana.*
Cultivar denomination: 'KERLATTE'.

BACKGROUND OF THE INVENTION

The present invention relates to a new and distinct cultivar of *Petunia*, botanically known as *Petunia×atkinsiana* and hereinafter referred to by the name 'Kerlatte'.

The new *Petunia* plant is a product of a planned breeding program conducted by the Inventors in Cambridge, United Kingdom. The objective of the breeding program is to create new uniform *Petunia* plants with attractive flower coloration that have good garden performance.

The new *Petunia* plant originated from a cross-pollination made by the Inventors in August, 2011 in Cambridge, United Kingdom of a proprietary selection of *Petunia×atkinsiana* identified as code number 10-423-01, not patented, as the female, or seed, parent with a proprietary selection of *Petunia×atkinsiana* identified as code number 10-423-02, not patented, as the male, or pollen, parent. The new *Petunia* plant was discovered and selected by the Inventors as a single flowering plant within the progeny of the stated cross-pollination in a controlled greenhouse environment in Cambridge, United Kingdom in May, 2012.

Asexual reproduction of the new *Petunia* plant by terminal vegetative cuttings in a controlled greenhouse environment in Cambridge, United Kingdom since September, 2012 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The new *Petunia* plant's phenotype may vary somewhat with variations in environmental conditions such as temperature and light intensity without, however, any variance in genotype.

The following traits have been repeatedly observed and are determined to be the unique characteristics of 'Kerlatte'. These characteristics in combination distinguish 'Kerlatte' as a new and distinct *Petunia* plant:

1. Mounding plant habit becoming more outwardly spreading with development.
2. Freely branching habit.
3. Moderately vigorous growth habit.
4. Early and freely flowering habit.
5. Medium-sized pale cream-colored flowers with dark purple-colored centers and venation.
6. Good garden performance.

Plants of the new *Petunia* can be compared to plants of the female parent selection. Plants of the new *Petunia* differ from plants of the female parent selection in the following characteristics:

1. Plants of the new *Petunia* are taller than plants of the female parent selection.
2. Plants of the new *Petunia* are more mounding than and not as trailing as plants of the female parent selection.
3. Plants of the new *Petunia* produce more cuttings per plant than plants of the female parent selection.
4. Plants of the new *Petunia* are more rain-tolerant than plants of the female parent selection.

Plants of the new *Petunia* can be compared to plants of the male parent selection. Plants of the new *Petunia* differ from plants of the male parent selection in the following characteristics:

1. Plants of the new *Petunia* are taller than plants of the male parent selection.
2. Plants of the new *Petunia* have smaller flowers than plants of the male parent selection.

3. Plants of the new *Petunia* flower earlier than plants of the male parent selection.
4. Flowers of plants of the new *Petunia* open fully whereas flowers of plants of the male parent selection do not open fully.

Plants of the new *Petunia* can be compared to plants of the *Petunia* 'Viva Cappuccino', not patented. In side-by-side comparisons conducted in Cambridge, United Kingdom, plants of the new *Petunia* differed from plants of 'Viva Cappuccino' in the following characteristics:

1. Plants of the new *Petunia* were more mounding than and not as upright as plants of 'Viva Cappuccino'.
2. Plants of the new *Petunia* had slightly smaller flowers than plants of 'Viva Cappuccino'.
3. Flowers of plants of the new *Petunia* opened fully whereas flowers of plants of 'Viva Cappuccino' did not open fully.

Plants of the new *Petunia* can also be compared to plants of the *Petunia×hybrida* 'Kerivoryvein', disclosed in U.S. Plant Pat. No. 23,812. In side-by-side comparisons conducted in Cambridge, United Kingdom, plants of the new *Petunia* differed from plants of 'Kerivoryvein' in the following characteristics:

1. Plants of the new *Petunia* were larger than plants of 'Kerivoryvein'.
2. Plants of the new *Petunia* were more low temperature-tolerant than plants of 'Kerivoryvein'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of typical plants of 'Kerlatte' grown in a container.

The photograph on the second sheet is a close-up view of a typical flowering plant of 'Kerlatte'.

The photograph on the third sheet is a close-up view of a typical flower of 'Kerlatte'.

DETAILED BOTANICAL DESCRIPTION

The aforementioned photographs and following observations, measurements and values describe plants grown in 30-cm containers, with three plants each, during the summer in a glass-covered greenhouse in Cambridge, United Kingdom and under cultural practices typical of commercial *Petunia* production. During the production of the plants, day temperatures ranged from 18° C. to 28° C., night temperatures ranged from 14° C. to 20° C. and light levels averaged 50 kilolux. Plants were pinched one time and were ten weeks old when the photographs and description were taken. In the following description, color references are made to The Royal Horticultural Society Colour Chart, 1995 Edition, except where general terms of ordinary dictionary significance are used.

Botanical classification: *Petunia×atkinsiana* 'Kerlatte'.

Parentage:

*Female, or seed, parent*.—Proprietary selection of *Petunia×atkinsiana* identified as code number 10-423-01, not patented.

*Male, or pollen, parent*.—Proprietary selection of *Petunia×atkinsiana* identified as code number 10-423-02, not patented.

Propagation:

*Type*.—By terminal vegetative cuttings.

*Time to initiate roots, summer*.—About seven days at temperatures about 20° C.

*Time to initiate roots, winter*.—About ten days at temperatures about 20° C.

*Time to produce a rooted young plant, summer*.—About 25 days at temperatures about 20° C.

*Time to produce a rooted young plant, winter*.—About 35 days at temperatures about 15° C.

*Root description*.—Fine, fibrous; white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Mounding plant habit becoming more outwardly spreading with development; freely branching habit with about six to seven primary lateral branches developing per plant; pinching enhances lateral branch development; moderately vigorous growth habit.

*Plant height*.—About 18 cm to 23 cm.

*Plant diameter*.—About 20 cm.

Lateral branch description:

*Length*.—About 29.3 cm.

*Diameter*.—About 4.1 mm.

*Internode length*.—About 2.6 cm.

*Strength*.—Moderately strong, flexible.

*Aspect*.—Upright to slightly spreading.

*Texture*.—Pubescent, hirsute.

*Luster*.—Dull.

*Color*.—Close to 144A.

Leaf description:

*Arrangement*.—Before flowering, alternate; after flowering, opposite; simple.

*Length*.—About 4.3 cm.

*Width*.—About 2.8 cm.

*Shape*.—Broadly elliptic.

*Apex*.—Acute.

*Base*.—Acute.

*Margin*.—Entire.

*Texture, upper surface*.—Slightly pubescent along veins and margins.

*Texture, lower surface*.—Slightly pubescent along veins and margins; protruding venation.

*Luster, upper and lower surfaces*.—Slightly glossy.

*Venation pattern*.—Pinnate; arcuate.

*Color*.—Developing leaves, upper surface: Darker than 146B. Developing leaves, lower surface: Close to 146C. Fully expanded leaves, upper surface: Darker than 146A; venation, close to 146C. Fully expanded leaves, lower surface: Slightly darker than 146B; venation, close to 144A.

*Petioles*.—Length: About 1.1 cm. Diameter: About 2.6 mm. Texture, upper and lower surfaces: Pubescent. Color, upper and lower surfaces: Close to between 144B and 145A.

Flower description:

*Flower arrangement and habit*.—Single-type salverform flowers arising from leaf axils; freely flowering habit with usually about 14 flower buds and flowers per lateral branch and about 81 flower buds and flowers per plant at one time; flowers face mostly outwardly.

*Fragrance*.—None detected.

*Natural flowering season*.—Plants flower continuously during the summer in the United Kingdom; early flowering habit, plants begin flowering about seven weeks after planting.

*Flower longevity*.—Individual flowers last about four to eight days on the plant; flowers not persistent.

*Flower diameter*.—About 4.8 cm.

*Flower depth* (*height*).—About 3 cm to 3.5 cm.

*Flower buds*.—Length: About 3.1 cm. Diameter: About 5.2 mm. Shape: Oblong. Color: Towards the base, close to 145A; towards the apex, close to 4B; venation, close to 187A.

*Corolla*.—Arrangement: Five petals fused at the base and opening into a flared trumpet. Petal length from throat: About 2 cm to 2.2 cm. Petal lobe width: About 2.5 cm. Petal shape: Spatulate. Petal apex: Obtuse with small central point. Petal margin: Entire, slightly sinuate and ruffled. Petal texture, upper surface: Smooth, glabrous. Petal texture, lower surface: Slightly pubescent; some protruding veins. Throat texture: Smooth, glabrous. Tube texture: Slightly pubescent. Petal color: When opening, upper surface: Close to 157A; venation, close to 79A and 200A; venation colors fading away from veins, close to 79B and 200B. When opening, lower surface: Close to 155D and 1D; main veins, close to 199A and 148A and lateral veins, close to 79A. Fully opened, upper surface: Close to 155A to 155B; venation, close to 79A to 79C; colors do not change with development. Fully opened, lower surface: Close to 155B and 11D; main vein, close to 199B and 144B and lateral veins, close to 86A. Throat: Darker than 79A; venation, darker than 79A. Tube: Close to 195A and 79A; venation, close to 195A and 79A.

*Calyx*.—Arrangement: One star-shaped calyx tube with five sepals fused at the base per flower. Sepal length: About 1.5 cm. Sepal width: About 3.2 mm. Sepal shape: Oblong. Sepal apex: Obtuse, blunt. Sepal margin: Entire. Sepal texture, upper and lower surfaces: Pubescent, coarse. Color, immature and mature, upper surface: Close to 146A. Color, immature and mature, lower surface: Close to 146B.

*Peduncles*.—Length: About 1.9 cm. Diameter: About 1.2 mm. Angle: About 45° to 60° from the stem axis. Strength: Moderately strong, flexible. Texture: Pubescent. Color: Close to 144A.

*Reproductive organs*.—Stamens: Quantity: Five per flower. Anther size: About 2 mm by 1.9 mm. Anther shape: Roughly round. Anther color: Close to 161B. Pollen amount: Abundant. Pollen color: Close to 158B to 158C. Pistils: Quantity: One per flower. Pistil length: About 2.3 cm. Style length: About 2 cm. Style color: Close to 144D. Stigma shape: Oval. Stigma color: Close to 144A. Ovary color: Close to 144A. Seeds and fruits: Seed and fruit development have not been observed on plants of the new *Petunia*.

Garden performance: Plants of the new *Petunia* have been observed to have good garden performance and tolerate wind, rain and temperatures ranging from about 4° C. to about 40° C.

Pathogen & pest resistance: Plants of the new *Petunia* have not been observed to be resistant to pathogens and pests common to *Petunia* plants.

It is claimed:

1. A new and distinct *Petunia* plant named 'Kerlatte' as illustrated and described.

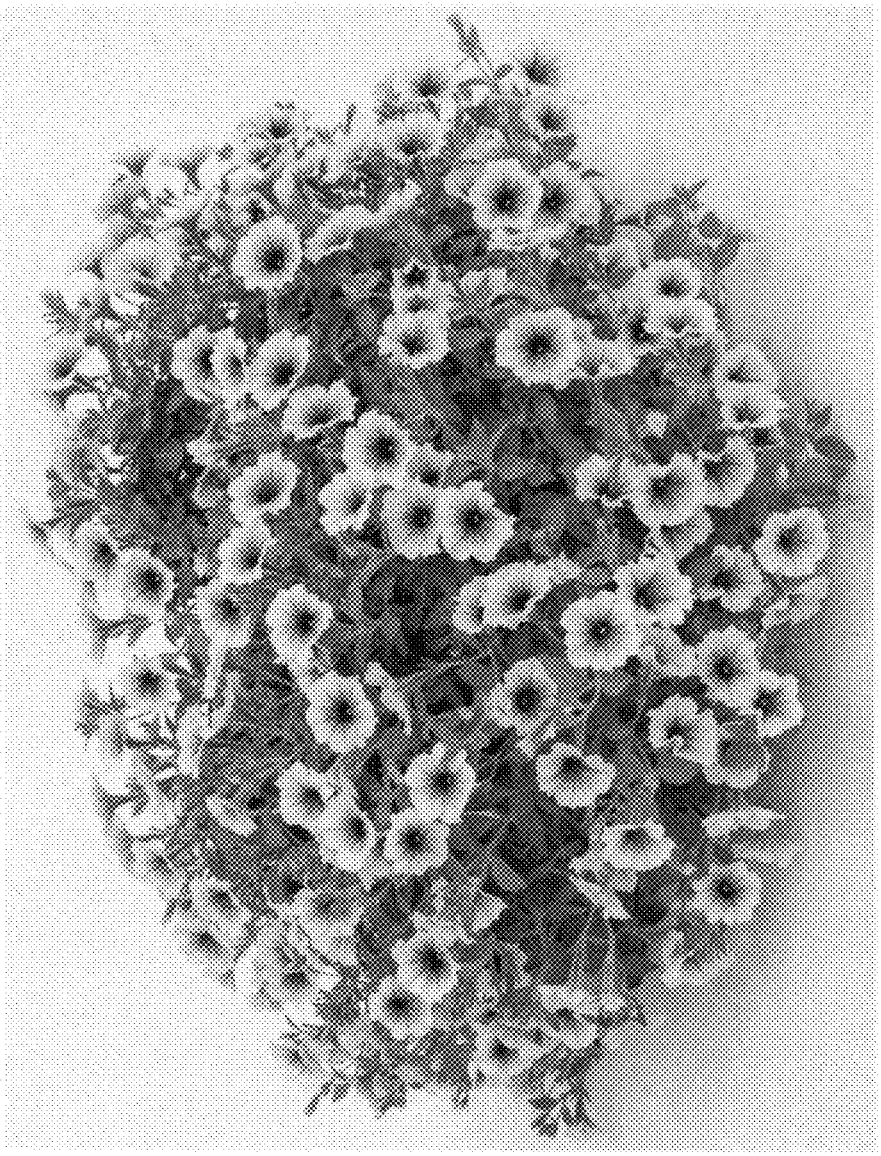

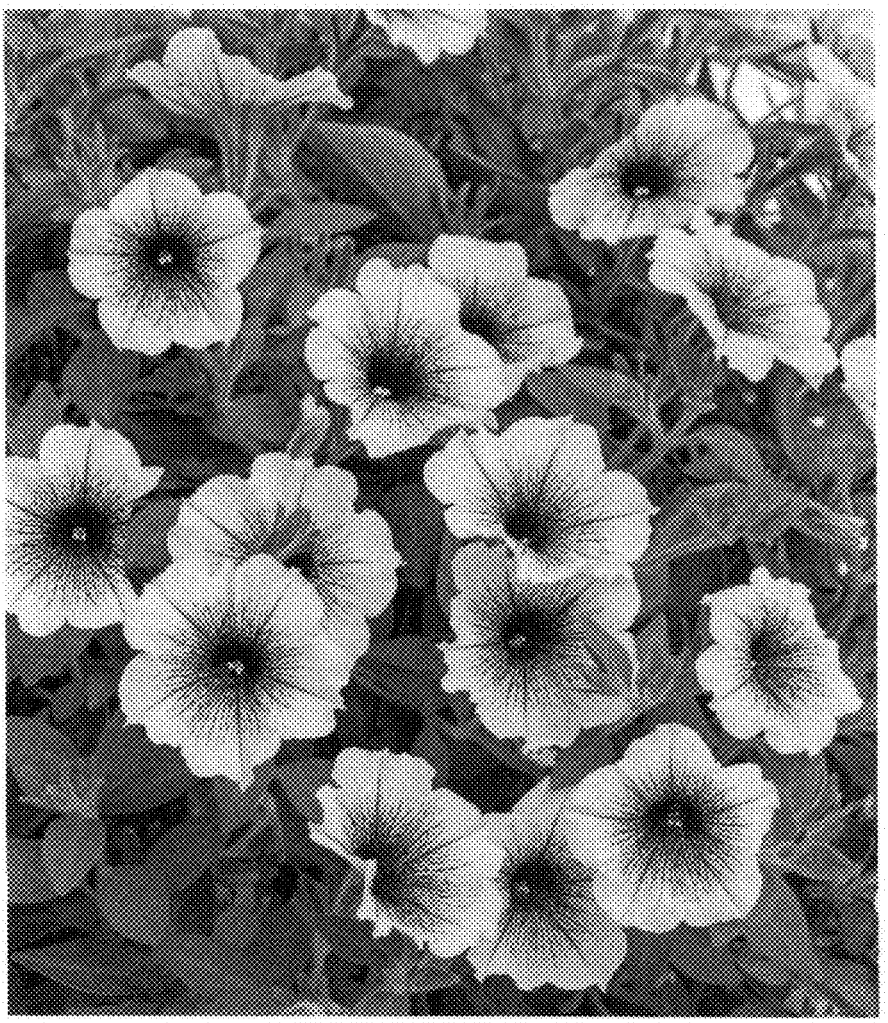

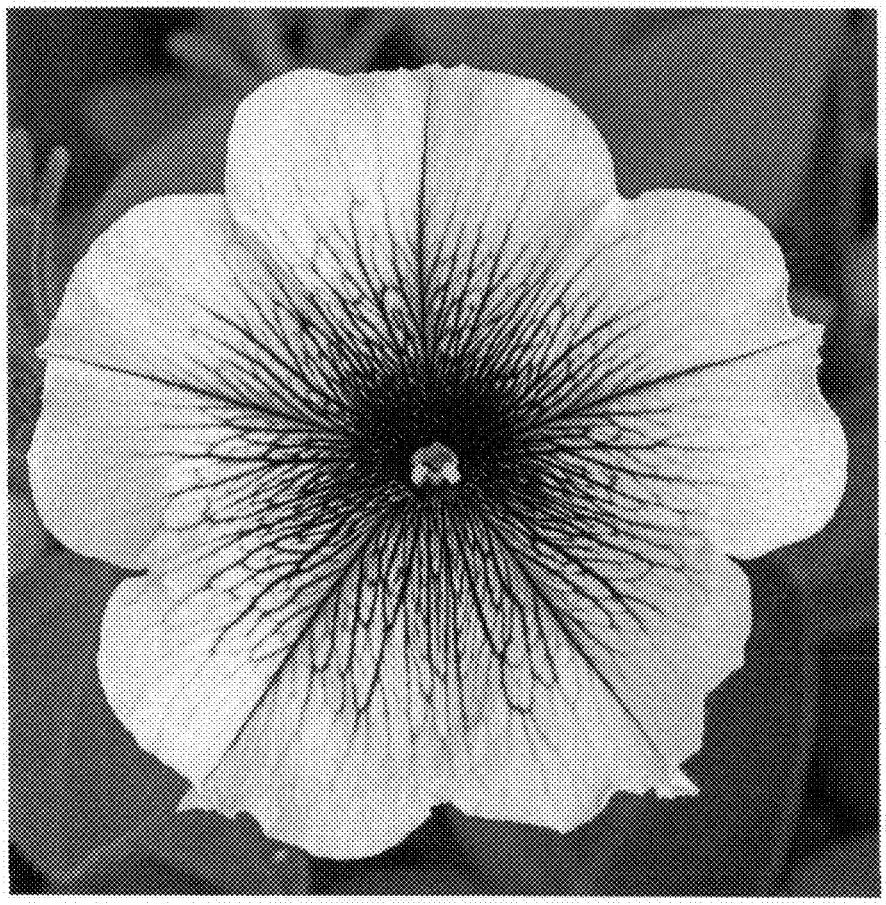

* * * * *